United States Patent [19]
Parsons

[11] Patent Number: 5,802,888
[45] Date of Patent: Sep. 8, 1998

[54] FLEXIBLE STRAP RESTRAINING DEVICE

[75] Inventor: Kevin L. Parsons, Appleton, Wis.

[73] Assignee: Arament Systems and Procedures, Inc., Appleton, Wis.

[21] Appl. No.: 600,563

[22] Filed: Feb. 13, 1996

Related U.S. Application Data

[63] Continuation of Ser. No. 327,042, Oct. 21, 1994, abandoned.

[51] Int. Cl.⁶ .......................... E05B 75/00; B65D 63/00
[52] U.S. Cl. .......................... 70/16; 24/16 PB; 128/879
[58] Field of Search ................... 70/16, 14, 15, 70/17, 18; 292/307 R, 307 A, 307 B, 319–325; 24/16 PB, 17 AP, 30.5 P, 484; 128/879

[56] References Cited

U.S. PATENT DOCUMENTS

| | | |
|---|---|---|
| 1,342,334 | 6/1920 | Kruger . |
| 1,456,846 | 5/1923 | Gamwell . |
| 1,746,890 | 5/1930 | Manacle . |
| 2,443,335 | 8/1948 | Vogel . |
| 3,027,665 | 4/1962 | St. John ................................ 24/17 AP |
| 3,107,395 | 10/1963 | Bundy . |
| 3,616,665 | 11/1971 | Rosenthal ................................ 70/16 |
| 3,875,771 | 4/1975 | Reisner . |
| 3,965,538 | 6/1976 | Caveney et al. ................. 24/16 PB |
| 4,071,023 | 1/1978 | Gregory ................................ 70/16 |
| 4,130,686 | 12/1978 | Takahashi et al. ............. 24/16 PB |
| 4,236,280 | 12/1980 | Kreiseder ....................... 24/16 PB |
| 4,532,679 | 8/1985 | Scott ................................ 292/307 R |
| 4,730,615 | 3/1988 | Sutherland ..................... 24/16 PB |
| 4,854,138 | 8/1989 | Charland . |
| 4,909,051 | 3/1990 | Lee ........................................ 70/16 |
| 4,910,831 | 3/1990 | Bingold . |
| 4,964,419 | 10/1990 | Karriker . |
| 5,007,257 | 4/1991 | Thompson .............................. 70/16 |
| 5,088,158 | 2/1992 | Burkholder ............................ 70/16 |
| 5,120,097 | 6/1992 | Fattori et al. ..................... 292/307 A |
| 5,159,728 | 11/1992 | Bingold ........................... 24/16 PB |
| 5,193,254 | 3/1993 | Geisinger ......................... 24/16 PB |
| 5,337,503 | 8/1994 | Goby ................................ 24/30.5 P |
| 5,367,419 | 11/1994 | Takeuchi .......................... 24/17 AP |
| 5,377,388 | 1/1995 | De Bever ............................. 292/319 |
| 5,377,510 | 1/1995 | Smith ............................. 24/16 PB |
| 5,385,373 | 1/1995 | Love ............................... 24/16 PB |
| 5,398,383 | 3/1995 | Bingold ........................... 24/16 PB |
| 5,443,155 | 8/1995 | Robinson .......................... 24/16 PB |

FOREIGN PATENT DOCUMENTS

| | | | |
|---|---|---|---|
| 2268778 | 1/1994 | United Kingdom ................ 70/16 |
| 8300676 | 3/1983 | WIPO .......................... 24/16 PB |

Primary Examiner—Darnell M. Boucher
Attorney, Agent, or Firm—McDonnell, Boehnen Hulbert & Berghoff

[57] ABSTRACT

An improved disposable double-loop restraining device is tamper resistant, utilizes a non-keyed lock and include a core material designed to resist friction cutting. A coded removable tab is provided for positively tracking a detainee with an arrest record. The device may be folded allowing large quantities to be easily stowed on the person of law enforcement personnel for mass arrest situations, and is brightly colored to assist in readily identifying detained individuals.

34 Claims, 5 Drawing Sheets

FLEXIBLE STRAP RESTRAINING DEVICE

This application is a continuation application of Ser. No. 08/327,042, filed Oct. 21, 1994, now abandoned.

BACKGROUND OF INVENTION

1. Field of Invention

The subject invention is generally related to restraining devices for use by law enforcement personnel and is specifically directed to an improvement in a disposable restraining device of the type having a flexible strap which forms two secure loops.

2. Description of Prior Art

Restraining devices such as handcuffs are well known and have been available for many years. The best known restraining devices are handcuffs consisting of a pair of metal rings which are placed about the wrists of an individual and locked into place. While traditional handcuffs serve the purpose of restraining an individual, they have a number of drawbacks. Conventional handcuffs are heavy, bulky to carry, expensive, require a key and are often inconvenient, particularly in multiple arrest situations such as riots and the like. Because of these drawbacks, it has become more and more desirable to design handcuffs which are lightweight, inexpensive and do not require a key. Moreover, it has become desirable to utilize disposable handcuffs, particularly in multiple arrest situations.

Disposable handcuffs are available which address some of the problems of conventional key-operated handcuffs. U.S. Pat. No. 4,964,419 entitled "Keyless Handcuffs", issued to R. L. Kariker on Oct. 23, 1990 and U.S. Pat. No. 4,854,138 entitled "Restraining Device", issued to Robert S. Charland on Aug. 8, 1989 illustrate two types of disposable handcuffs.

The subject invention is specifically directed to an improvement in the type of disposable handcuffs generally described in U.S. Pat. No. 4,910,831 entitled "Two-Loop Law Enforcement Restraining Device Formed From A Single, Flat Strap" issued to Richard F. Bingold on Mar. 27, 1990. This double-loop disposable restraining device is formed from a single flexible strap and is lightweight and inexpensive. It is designed to be removed from the restrained person by cutting the strap.

While such prior art double-loop disposable handcuffs meet the functional requirements of a restraining device, a major disadvantage is that a detainee can release himself by tampering with the device. For example, the prior art plastic disposable handcuffs may be friction cut by vigorously rubbing a piece of string or twine against the strap until sufficient heat is generated to cut through the plastic. Thus, a detainee may hold his shoelace in his teeth and vigorously rub the strap against his shoelace until the strap reaches the melting point, at which point the shoelace cuts through the strap and frees the detainee.

Also, the locking area of most disposable handcuffs consists of a pair of socket clasps with an opening containing a locking wedge which projects into the opening and secures the loops, in much the same manner as garbage bag ties and the like. Many disposable handcuffs may be released by using a small thin piece of wire or a pin or nail to wedge underneath the locking area of the handcuff. Typically, the wire is fed in from the front side of the locking area and is used to shim open the locking wedge, allowing the strap to be withdrawn and releasing the handcuffs.

Further, there has been a movement toward using disposable handcuffs due to the increasing concern of the spreading of AIDS, as well as Hepatitis, since restrained individuals who struggle violently often create open wounds which result in blood on the handcuffs. Disposable handcuffs assure that the handcuffs will not be reused and thereby create a carrier for communicable diseases through contamination due to cuts or abrasions received during the detainment. Even the edges of many prior art disposable handcuffs are similar to the sharp edges of traditional handcuffs made of metal. Sharp edges may cut wrists of the detainees and may even cause injury to the officer using the handcuffs.

While the prior art disposable handcuffs are lightweight in comparison to conventional metal handcuffs, another disadvantage is that they are too bulky for a large quantity to be carried on a day-to-day basis. In certain situations, such as a multiple arrest applications, law enforcement personnel may be required to carry a substantial number of handcuffs. Because of their length and resilience, the current disposable restraining devices do not permit law enforcement personnel to readily carry a large number of handcuffs on their person. Further, there is often a need to have handcuffs concealed by plainclothes personnel or even uniformed officers on regular duty. The common practice of concealing handcuffs on the inside of a belt or in other clothing, as with traditional handcuffs, is not possible with the current disposable handcuffs because of their length.

In addition, while the prior art disposable handcuffs may meet the basic functional requirements of a restraining device, the color of the handcuffs makes it difficult to identify at a glance or at a distance whether an individual has been handcuffed when a group of individuals are detained, particularly in the common situation wherein the arrest takes place in a darkened area. The prior art disposable handcuffs are usually black, white or neutral in color and sometimes blend into the skin or clothing of the individual. It is important that law enforcement personnel be able to readily identify what portion of a group of individuals, such as gang members, demonstrators, rioters or the like, have been handcuffed.

In addition, particularly in multiple arrest situations, it is often difficult to trace each individual to the written arrest record for later processing. Currently, law enforcement personnel must track arrested and detained individuals with a written arrest record which is processed after the detainee is transported from the scene of the arrest. This is very difficult in a multiple arrest situation where many individuals are detained and many records are generated. Tying the record to the person is a difficult cumbersome and sometimes impossible task. The improper tracking of an arrest record often leads to dismissal of charges because of inability to tie paperwork to a particular individual.

Therefore, there is a need for an improved, disposable double-loop restraining device which prevents a detainee from either releasing or injuring himself, assists law enforcement personnel in identification and tracking of detainees and is easily stowed and readily accessible in large quantities, particularly in mass arrest situations.

SUMMARY OF THE INVENTION

The subject invention is directed to an improved disposable double-loop restraining device which is tamper resistant, utilizes a non-keyed lock, and includes means for positively tracking a detainee with the arrest record. The device is easily stowed, allowing large quantities to be carried for mass arrest situations and may include a multi-fold design for further compact storage. In addition, the device may be brightly colored to assist law enforcement personnel in readily identifying detained individuals. It is specifically designed to minimize injury to both detainee and law enforcement personnel.

In the preferred embodiment of the invention, the flexible strap includes a core material which is specifically designed to prevent the detainee from cutting or melting through the strap by vigorously rubbing it against a piece of string, such as his shoe lace or the like. Although any material having a higher melting point than the strap may be used as the core material, it may be desirable to use a woven fiber material, such as Kevlar brand strands, that is not sensitive to heat. Also, a metallic wire may be used.

The preferred embodiment of the invention also includes a unique locking mechanism having an extended locking wedge with a design for preventing the detainee from using a wire to shim open the lock to release himself. Further, the subject invention may include a double lock feature making it virtually impossible to pick or shim open the handcuff. The invention also may include an integral hinge located in the center of the strap increasing the stowability of the device and providing law enforcement personnel with a convenient means of carrying it by permitting it to be placed in the uniform belt. In order to reinforce the hinge area, the invention may also include an auxiliary sliding cover which slides onto the strap and is selectively movable into a position over the top of the hinge area. In addition to reinforcing the hinge area, the sliding cover provides further protection against tampering of the lock area after the handcuffs are applied to a detainee. Additionally, the device may include means for further folding the device in a compact manner and maintaining it in the folded position.

The preferred embodiment of the subject invention also may include a removable tab containing an identification code which matches the code permanently affixed on the flexible strap restraining device. The removable tab may include an adhesive backing so that it may be readily attached to the arrest record. The strap of the subject invention may also include a write-on surface for use with a ball point pen, such as, by way of example, the write-on strip provided on credit cards. The write-on surface will allow police officers to readily identify subjects using equipment that a police officer commonly has on hand.

In addition, the restraining device may be made in a neon or other bright color finish. The brightly colored, distinctive restraining devices of the present invention provide law enforcement personnel with a means for readily identifying those individuals in a group which have been secured and detained. Also, the invention incorporates the use of smooth, radiused edges to minimize abrasion and cutting injuries to the detainee.

Therefore, it is an object and feature of the subject invention to provide improvements in disposable restraining devices while maintaining the desirable weight, costs and utilization features of the prior art.

It is also an object and feature of the subject invention to provide a disposable restraining device of a design resistant to friction or heat cutting.

It is a further object and feature of the subject invention to provide a disposable restraining device which has an identification system for tracking an individual who has been arrested.

It is a further object and feature of the subject invention to provide a disposable restraining device having a tamper resistant non-keyed lock.

It is yet another object and feature of the subject invention to provide a disposable restraining device which is easily stowable within the person of the law enforcement officer.

It is yet another object and feature of the subject invention to provide a disposable restraining device which includes a multi-fold design and also includes an element for reinforcing and further protecting the center fold area.

It is a further object and feature of the subject invention to provide a disposable restraining device which stands out for readily identifying detained individuals.

Other objects and features will be readily apparent from the accompanying drawings and description.

DETAILED DESCRIPTION OF THE PREFERRED EMBODIMENT

Figure 1:
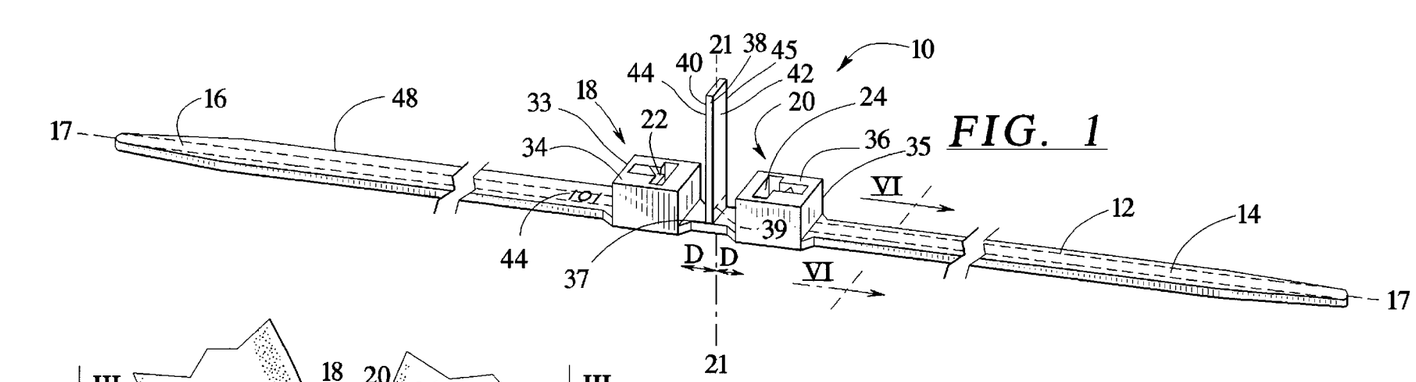
FIG. 1 is a perspective view of an elongated flexible strap restraining device in accordance with the present invention.
Figure 4:
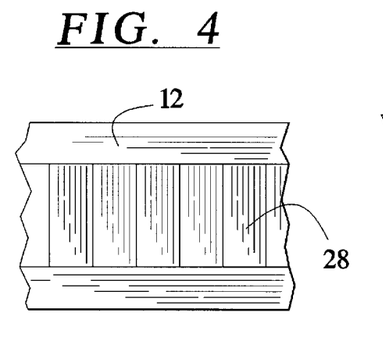
FIG. 4 is a fragmentary plan view of the strap, showing the saw-tooth locking ribs.

Referring specifically to FIG. 1 of the drawings, a flexible strap restraining device embodying the present invention is designated generally by the reference numeral 10 and comprises a single elongated, substantially flat straight strap 12 having two outer free ends 14 and 16. The ends may be tapered to facilitate quick alignment of the strap within the lock system, in the manner well known to those skilled in the art. The strap 12 is preferably made of an inexpensive, lightweight, strong, stiffly flexible, plastic material similar to wire ties and bag ties, and the surface of the strap consists of plurality of saw tooth ribs 28 (see FIG. 4). The strap contains a core material, such as the metal wire 15, imbedded in the body of the strap and extending the length of the strap along centerline axis 17 (FIG.1). Since the core has a higher melting point than the strap, a detainee may not cut the strap by vigorously rubbing a piece of string or twine, such as his nylon shoelace, against the strap until sufficient heat is generated to melt and cut through the strap. If he attempts this, he will cut to the core and then the core will cut the shoelace.

Figure 2:
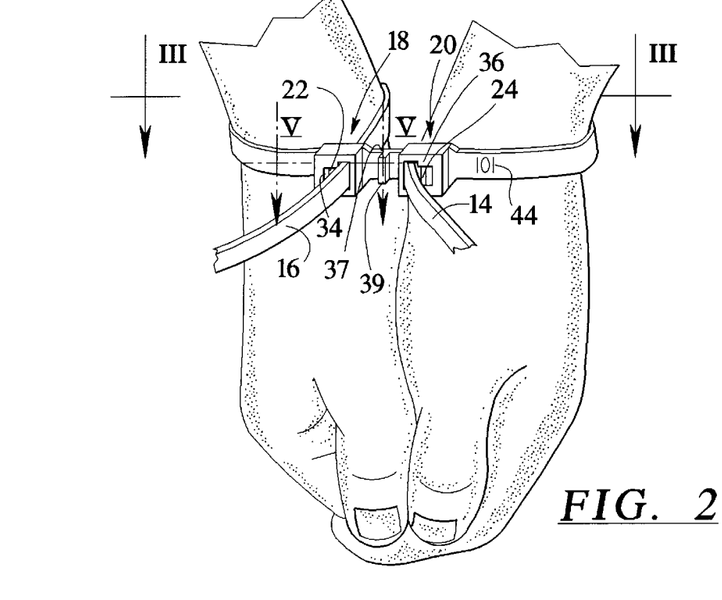
FIG. 2 is a perspective view of the flexible strap restraining device as applied as a handcuff restraint.
Figure 3:
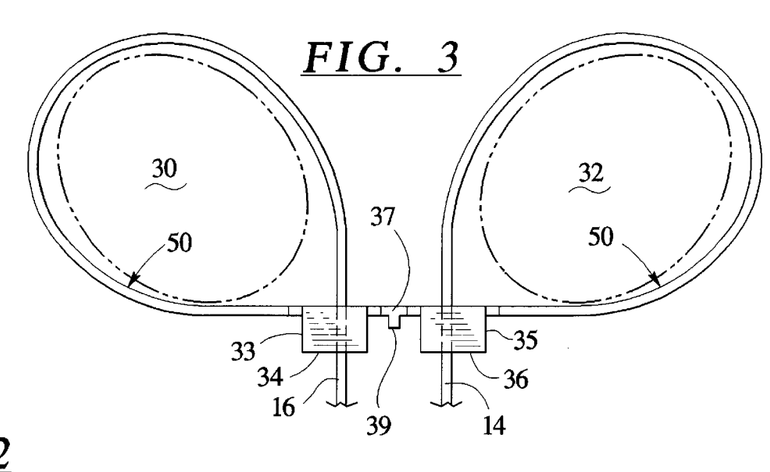
FIG. 3 is a side plan view illustrating the ends of the strap bent and inserted into the locking system for forming a double loop restraining device.
Figure 5:
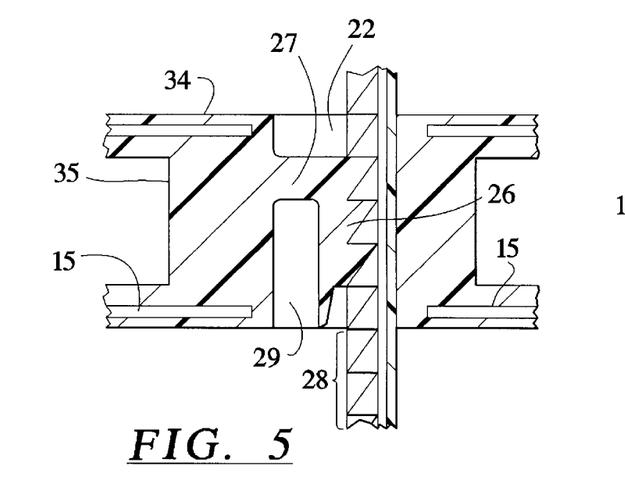
FIG. 5 is an enlarged cross sectional view taken along line 5—5 of FIG. 2 and showing the locking clasp with the strap inserted in and engaged by the extending locking wedges.
Figure 6:
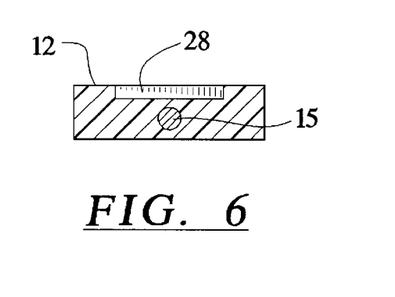
FIG. 6 is across sectional view of the strap taken along line 6—6 of FIG. 1.

The first preferred embodiment of the strap includes a pair of locking blocks 18 and 20, respectively, which are located an equal distance D from the center line 21 located midway between the two outer ends 14 and 16 of the strap (see FIG.1). Each locking block comprises a prosecuting box with a top surface 34 and 36 and outer walls 33 and 35 (FIGS. 1 and 5). The locking blocks 18 and 20 have central openings 22 and 24 as seen in FIGS. 1 and 5. As shown in FIG. 2, the ends 14 and 16 are employed by encircling the detainee's hands and inserting each end through locking blocks 18 and 20 to form a pair of closed loops. As shown in FIG. 5, the interior of each box is hollow and includes an integral resilient spring 27 and saw-tooth wedge locking surface 26. As best seen in FIG. 5, the spring is secured to outer wall 33 and projects into the central opening 22. The saw-toothed wedge surface 26 is connected to the spring 27. The wedge surface 26 is adapted to resiliently engage the saw-tooth ribbed surface 28 of the respective strap and retain the strap once it has been inserted into central openings 22 and 24 (FIGS. 3 and 5) and pulled into two loops 30 and 32 as shown in FIG. 3. In the first preferred embodiment, the saw teeth of the wedge surface 26 are extended and projected in a downward direction (as drawn). The extended wedges prevent the forcing of the saw teeth of the wedge surface 26 in the opposite direction and releasing the lock. As shown in FIG. 5, the gap 29 between the outer wall 33 and the extended saw tooth wedge surface 26 permits the wedge surface 26 to move and allows the respective strap to be inserted. The resilient spring 27 assures that the wedge surface 26 will be urged into the saw-tooth ribbed surface 28 of the strap and lock the restraining device. In the first preferred embodiment, the spring 27 is uniquely positioned to form a cover or shield for wedge surface 26, minimizing tampering by substantially covering the locking mechanism, making it difficult to release the lock through insertion of a wire or pin into top surfaces 34 and 36 of the lock to force the wedge surface 26 out of engagement with the strap. When using the lock system of the first preferred embodiment, the restraining device 10 must be cut off in order to release the detainee.

Figure 7:
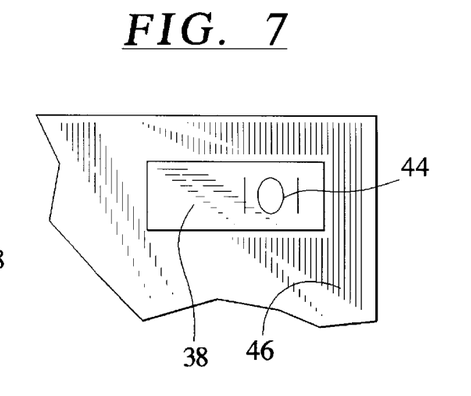
FIG. 7 shows the removable tab as attached to a typical arrest document.
Figure 8:
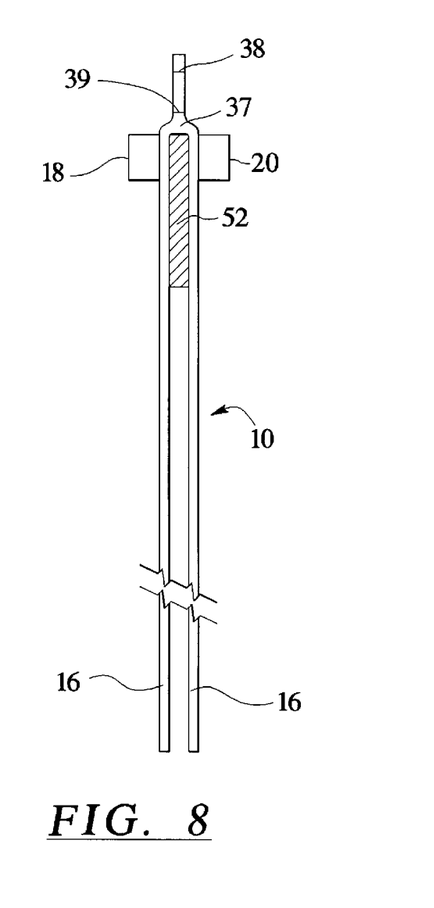
FIG. 8 is a plan view illustrating the restraining device of the invention in a position to be stowed on the uniform belt of an officer.

An integral, live hinge 37 is located at center 21 (FIG. 1) and permits the strap to be folded (FIG. 8). In the first preferred embodiment, the integral hinge 37 acts as a bridge between the two loops and also serves as a holder for removable tab 38. It is contemplated that the core material would extend through the hinge. The tab 38 may be scored or perforated at 39 (FIG. 1) and is removable from the strap by tearing. In the first preferred embodiment, the removable tab has a front side 40 containing an identification code 44, such as 101 or other alpha-numeric sequence, and a back side 42 containing an adhesive material covered by a strippable protective shield 45. The removable shield protects the adhesive backing against soiling or premature activation. The identification code 44 is also permanently affixed to the strap 12 in a position permitting the code to be viewed when the strap is formed into loops 30 and 32 (FIGS. 1 and 3). In use, the removable tab 38 is detached from the strap along the perforation 39 and may be attached to an arrest record document 46 or the like (FIG. 7) to assist in tracking detainees with the written record.

As shown in FIG. 8, the strap restraining device 10 is ideally suited for stowing in a ready position on the belt 52 of a law enforcement uniform. The strap may be folded at hinge 37 and looped over belt 52. This permits a plurality of straps to be carried, which is particularly important in multiple arrest situations. The officer may use tab 38 to grasp and remove the strap from the belt. Once the restraining device has been employed, the tab may be removed and attached to an arrest record to track the individual processing.

In the first preferred embodiment, the flexible strap 12 is made of a material 48 having a neon or bright color surface for enabling law enforcement personnel to easily identify the individuals who are handcuffed. Also, in the first preferred embodiment, the edges 50 of the strap will have a slight radius to prevent wrist injury or abrasion.

Figures 9, 10, 11:
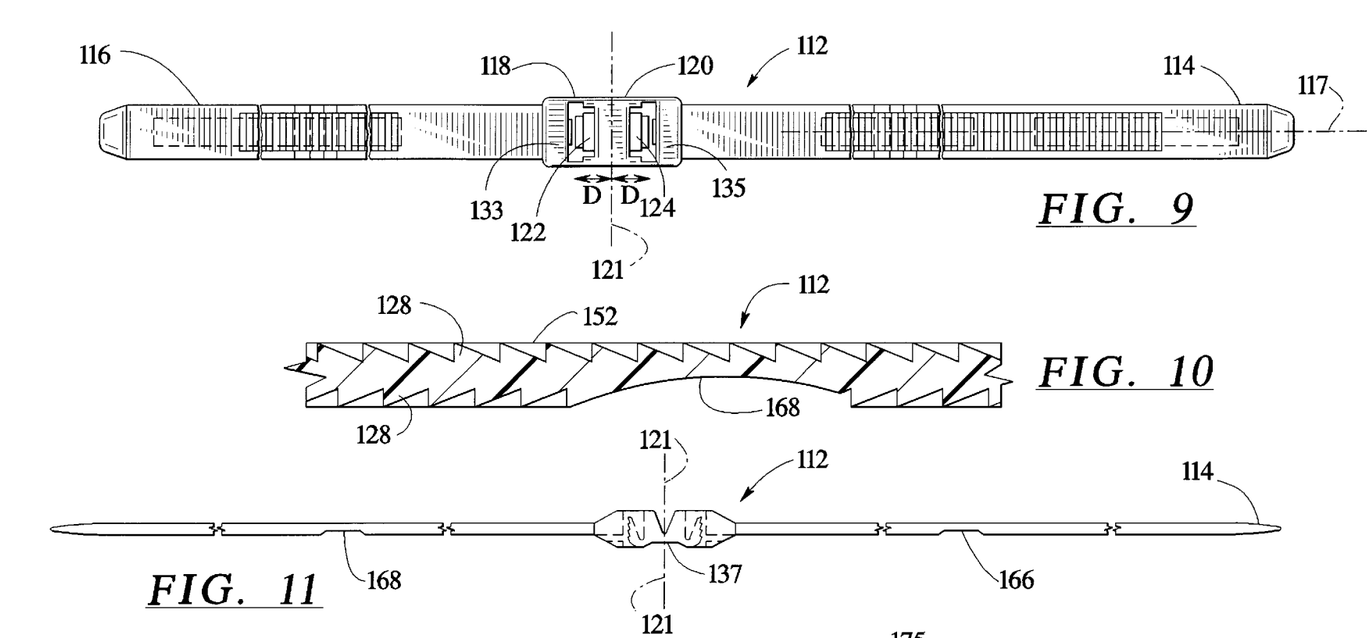
FIG. 9 is a plan view of an alternative preferred embodiment of the elongated flexible strap restraining device.
FIG. 10 is an enlarged side view of the saw-tooth ribbed surface on both sides of the strap and the bend for folding the strap.
FIG. 11 is a plan view of the strap showing the hinge for folding the strap in half and the bends for further folding the strap.

An alternative preferred embodiment of the subject invention is shown in FIGS. 9 to 14. Referring specifically to FIG. 9, a flexible strap restraining device of the second preferred embodiment is designated generally by the reference numeral 110 and comprises a single elongated, substantially flat straight strap 112 having two outer free ends 114 and 116. The ends may be tapered to facilitate quick alignment of the strap within the lock system, in the manner well known to those skilled in the art. The strap 112 is preferably made of an inexpensive, lightweight, strong, stiffly flexible, plastic material similar to wire ties and bag ties, and has a top surface 152 and a bottom surface 154. Both the top and bottom surfaces of the strap consist of plurality of saw tooth ribs 128 (see FIG. 10). The strap contains a core material having a higher melting point than the strap, such as the woven fiber 115, imbedded in the body of the strap and extending the length of the strap along centerline axis 117 (FIG. 9). As in the first preferred embodiment, a detainee may not cut the strap by vigorously rubbing a piece of string or twine, such as his nylon shoelace, against the strap since if he attempts this, he will cut to the core and then the core will cut the shoelace.

Figures 12, 13:
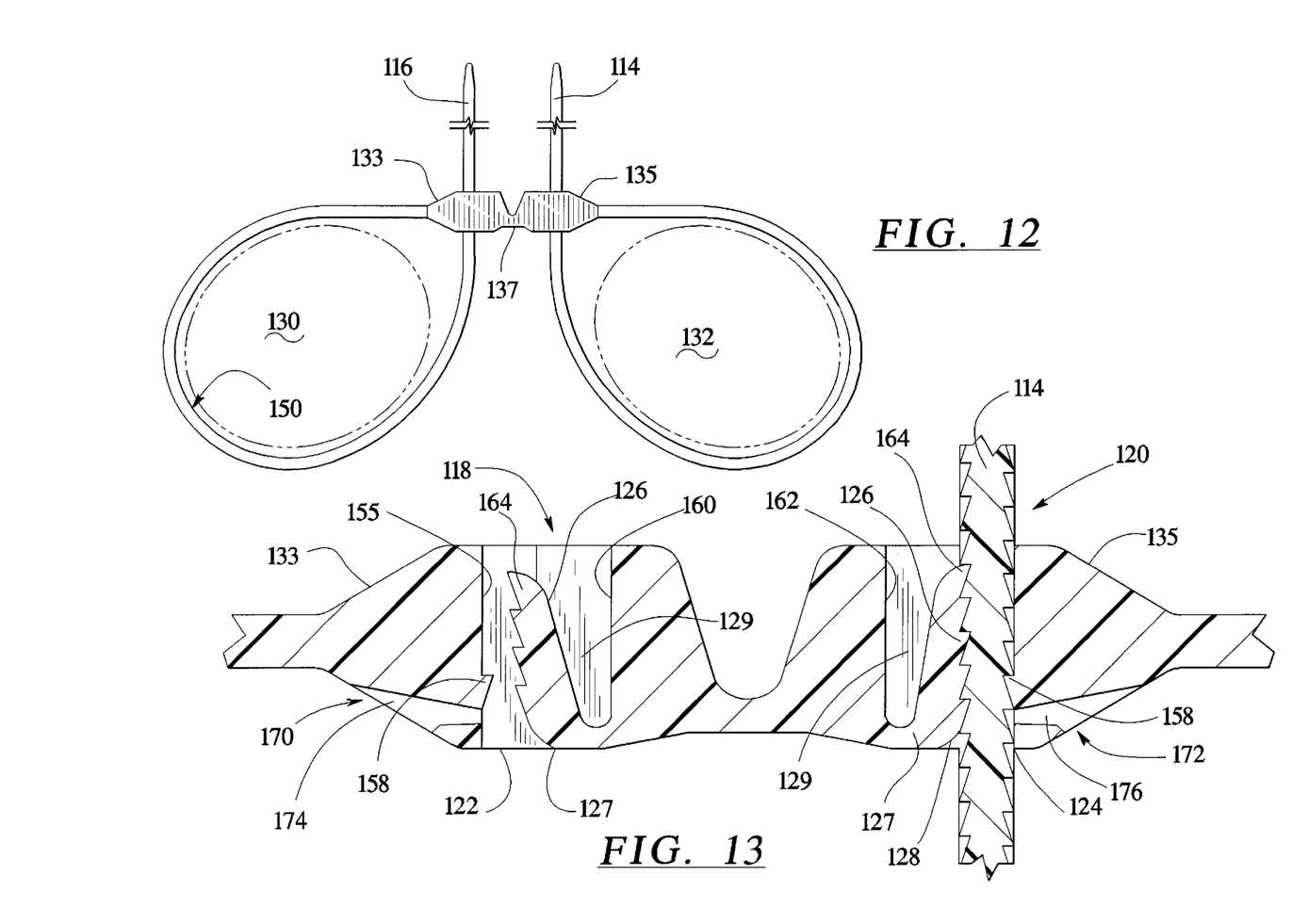
FIG. 12 is a side plan view illustrating the ends of the strap inserted into the locking system for forming a double loop restraining device.
FIG. 13 is an enlarged cross-sectional view showing the locking mechanism including a rounded edge on the extended locking wedges and an additional tooth opposite the locking wedges.

The alternative preferred embodiment of the strap includes a pair of locking blocks 118 and 120, respectively, which are located an equal distance D from the center line 121 located midway between the two outer ends 114 and 116 of the strap (see FIG. 9). Each locking block comprises a prosecuting box with a top surface 134, 136, outer wall 133, 135 and inner wall 160, 162, respectively (FIG. 13). The locking blocks 118 and 120 have central openings 122 and 124 as seen in FIGS. 9 and 13. As shown in FIG. 13, the interior of each box is hollow and includes an integral resilient spring 127, a saw-tooth wedge locking surface 126 and an interior wall 155 opposite from the wedge surface 126. As best seen in FIG. 13, the spring is secured to inner walls 160 and 162, respectively, and projects into the central openings 122 and 124. The saw-toothed wedge surface 126 is connected to the spring 127. The wedge surface 126 is adapted to resiliently engage the saw-tooth ribbed surface 128 of the respective strap and retain the strap once the ends 114, 116 have been inserted into central openings 122 and 124 (FIG. 13) and pulled into two loops 130 and 132 (FIG. 12) As shown in FIG. 13, the gap 129 between the outer wall 133 and the extended saw tooth wedge surface 126 permits the wedge surface 126 to move and allows the respective strap to be inserted. The resilient spring 127 assures that the wedge surface 126 will be urged into the saw-tooth ribbed surfaces 128 of each end of the strap and lock the restraining device.

As in the first embodiment, the saw teeth of the wedge surface 126 of the alternative preferred embodiment are extended to prevent the forcing of the saw teeth of the wedge surface 126 in the opposite direction and releasing the lock. Also, the spring 127 is positioned to form a cover or shield for wedge surface 126, minimizing tampering by substantially covering the locking mechanism, making it difficult to release the lock through insertion of a wire or pin into top surfaces 134 and 136 of the lock to force the wedge surface 126 out of engagement with the strap.

In addition, a locking tooth 158 is included in each of the locking blocks 118, 120 on the interior wall 155 opposite from the wedge locking surface 126 (see FIG. 13). Thus, the ends 114, 116 of the strap 112 are inserted into central openings 122 and 124 and are engaged by teeth on both sides of the strap. This double locking feature makes it virtually impossible to release the lock through insertion of a wire or pin into top surfaces 134 and 136. In fact, insertion of a wire or pin between the strap 112 and the wedge surface 126 would actually force the locking tooth 158 on the interior wall 155 into a tighter locking position on the strap. In addition, as shown in FIG. 13, the wedge locking surface 126 includes a rounded top end 164. By rounding the top end 164 of the wedge locking surface 126, it becomes very difficult for someone using an ice pick or similar sharp object to try and hook the end or the strap and pry it back. Moreover, prying the strap back in either direction will not release the strap since it will be engaged by either the saw tooth wedge surface 126 or the locking tooth 158 and therefore is locked in place. When using the double lock system of the second preferred embodiment, the restraining device 110 must be cut off in order to release the detainee.

An integral, live hinge 137 is located at center 121 (FIG. 11) and permits the strap to be folded in half. In the preferred embodiment, the integral hinge 137 acts as a bridge between the two loops. It is contemplated that the core material would extend through the hinge. As shown in FIGS. 10 and 11, the strap further includes a thinner section forming a first bend 166 located midway between the outer end 114 and the center line 121 and a second bend 168 located midway between the outer end 116 and the center line 121. By folding the straps in half at bends 166 and 168, and then folding the handcuff in half at the hinge 137, a compact, easily carried restraint is created. In addition, the second preferred embodiment includes pockets 170 and 172 (FIG. 13) for securing the handcuff in the tri-folded position. As shown in FIG. 13, locking boxes 118 and 120, include channels 174 and 176 on outer walls 33 and 35 to form pockets 170 and 172. The ends 114 and 116 of the strap 112 are inserted into the pockets 170 and 172, respectively, and form a wedge fit. By nature of the wedge fit of the pockets and the manner in which they are positioned, placing the ends 114 and 116 of the strap into the pockets 170 and 172 actually locks the handcuff in a folded position.

Figure 14:
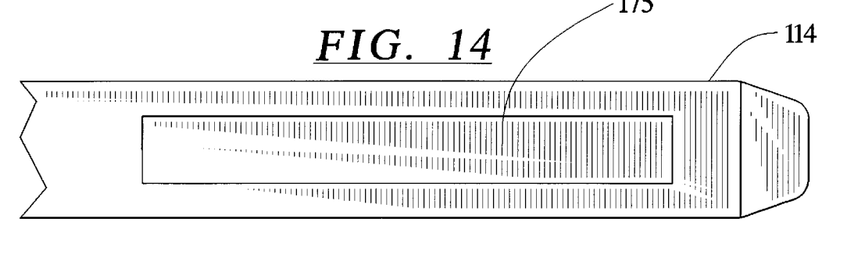
FIG. 14 is an enlarged plan view showing the write-on surface on the strap.

The alternative preferred embodiment also includes a write on surface 175 (see FIG. 14). The write-on surface is located on either end 114 or 1lo and is visible when the strap is formed into two closed loops. The write-on surface consists of a strip made from material similar to the material used on credit cards. By providing a write-on surface similar to that used by credit card companies, the police officer may readily identify subjects with a commonly carried ball point pen and does not need a special marker.

As in the first preferred embodiment, the flexible strap 112 is made of a material 148 having a neon or bright color surface for enabling law enforcement personnel to easily identify the individuals who are handcuffed. Also, in the second preferred embodiment, the edges 150 of the strap will have a slight radius to prevent wrist injury or abrasion.

Figures 15, 16, 17:
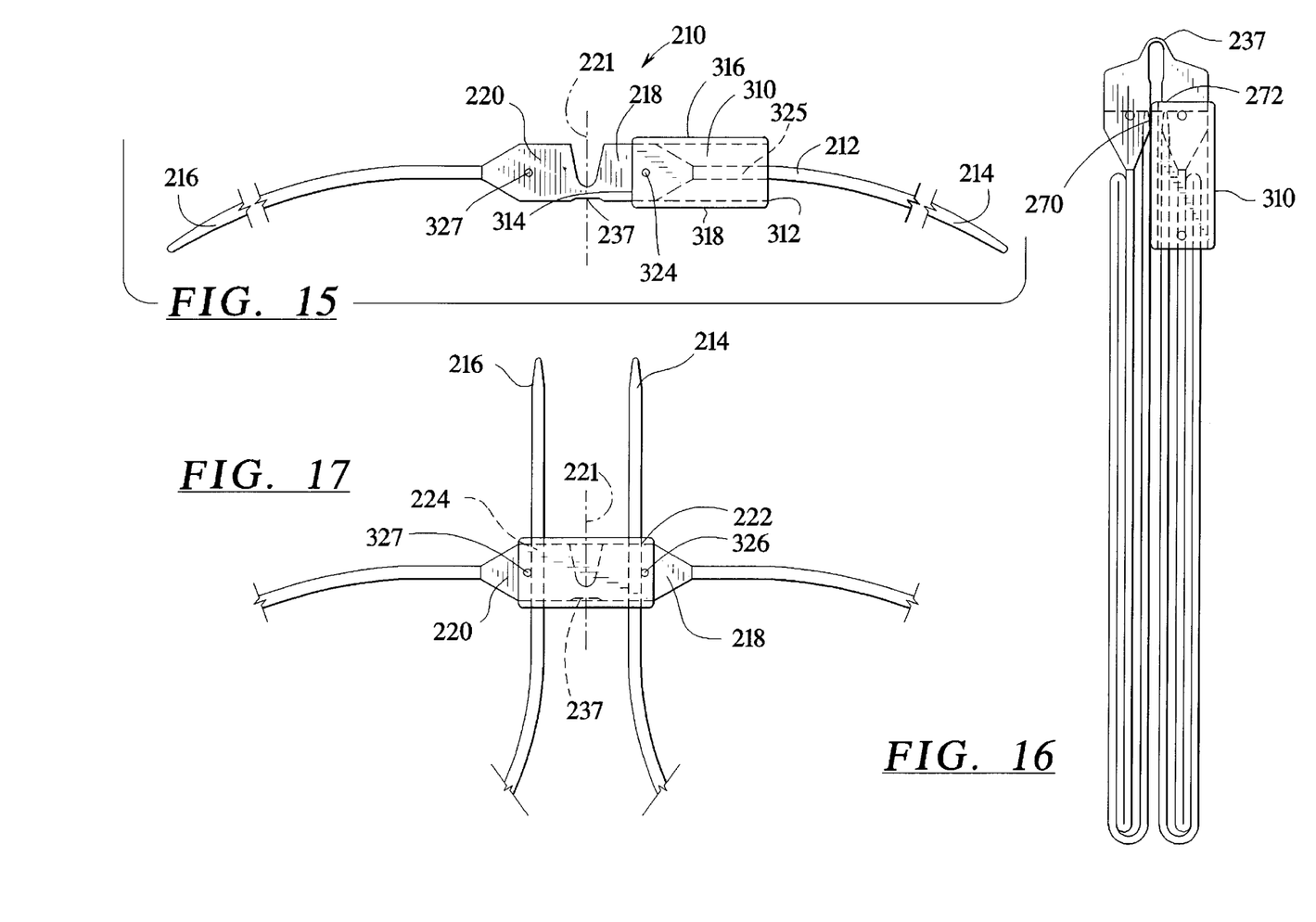
FIG. 15 is a perspective view of the locking mechanism with a sliding cover in a storage position adjacent to the hinge and partially covering one locking mechanism.
FIG. 16 is a side view of the restraining device folded in half at the hinge and showing a multi-folded storage position with the cover securing a folded end of the strap in the multi-folded position.
FIG. 17 is a plan view illustrating the cover in its operational position over the hinge area and the ends of the strap inserted into the locking system and cover.

FIGS. 15–17 illustrate a third preferred embodiment of the invention. As in the first and second preferred embodiments, the restraining device 210 comprises a single elongated, substantially flat strap 212 which includes outer ends 214, 216, a saw tooth surface and a core material, imbedded in the body of the strap, with a higher melting point than the material of the strap. An integral, live hinge 237 is located at center 221 (FIGS. 15 and 16) and permits the strap to be folded in half. In the preferred embodiment, the integral hinge 137 acts as a bridge when the strap is formed into loops.

The strap also includes a pair of locking blocks 218 and 220, respectively, which are located an equal distance D from the center line 221 located midway between the two outer ends of the strap. The locking blocks 218 and 220 have central openings 222 and 224 in which the outer ends 214, 216 of the strap are inserted. As in the first and second preferred embodiments, the locking blocks are designed to minimize tampering and make it difficult to release the lock through insertion of a wire or pin into the openings 222, 224 of the lock blocks to forcibly release the strap.

The third preferred embodiment of the invention includes a cover 310 which may be positioned over the locking blocks 218 and 220 to reinforce the area where the hinge 237 is located (FIG. 17). The cover 310 has a hollow interior, interior walls and opposite open sides, 312, 314 and top and bottom portions, 316 and 318. The cover 310 includes slots 320 and 322 which extend through the top and bottom portions, 316, 318 of the cover. The cover 310 is placed on the restraining device by inserting one end of the strap through the open side 312 and sliding the cover to a position over the locking blocks 218, 220 into the reinforcing, operational position.

When the cover 310 is in the operational position, the slots 320, 322 are aligned with the central openings 222, 224. The strap is formed into the restraining loops by inserting the ends 214, 216 of the strap through the slots 320, 322 and the central openings 222, 224 (see FIG. 17). Thus, when the restraining device is applied to the detainee, the cover is moved to its operational position to structurally reinforce the area where the hinge 237 is located and help prevent the strap from breaking when force is applied to the hinge. In addition, in its operational position, the cover 310 provides further protection from tampering with the locking mechanism of the device.

As shown in FIG. 15, when the cover 310 is not in use, it may be stored on the strap adjacent to the hinge in a position which partially overlaps one locking box. In order to secure the cover 310 in either the storage or operational position, the third preferred embodiment may include a retaining system, such as a detent lock, for securing the cover in place. The cover 310 includes at least one protrusion on its interior walls which extends into the interior of the cover to slidably engage a corresponding recess on each locking box. In the preferred embodiment, the cover 310 includes a pair of protrusions 324, opposite one another on the interior walls, located near one open side of the cover and a second pair of protrusions 325, opposite one another on the interior walls, located near the opposite open side of the cover. Each locking box 218 and 220, includes a pair of corresponding recesses 326 and 327, adapted to receive the protrusions.

The cover 310 slides over the strap until the protrusions 324 on the cover and the recesses 326 on the locking box are placed in contact with each other. When the cover is moved to a position adjacent to the hinge and partially overlapping one locking box, the protrusions 324 is engaged with the recesses 326 of the locking block and the cover is secured in the storage position. If the cover is slidably moved beyond the initial engagement of the protrusions 324 and recesses 326 to its operational position over both locking boxes, the protrusions 325 and recesses 327 of the second locking box are also engaged thereby securing the cover 310 in the operational position.

As seen in FIG. 16, the strap may be secured in a multi-folded position. The strap of the third preferred embodiment may include a plurality of thinner sections forming bends 330 allowing the strap to be multi-folded (FIGS. 16 and 17). The locking blocks 218 and 220 may include channels to form pockets 270 and 272. As in the second preferred embodiment, the ends 214, 216 of the multi-folded strap may be inserted into the pockets 270 and 272 to form a wedge fit and maintain the strap in the folded position. In addition, as shown in FIG. 16, the hollow interior of the cover 310 may be adapted to receive and form a wedge fit with a folded portion of the strap to further maintain the strap in the multi-folded position.

While certain features and embodiments of the invention have been described in detail herein, it will be readily understood that the invention includes all modifications and enhancements within the scope and spirit of the following claims.

What is claimed is:

1. In a disposable retraining device having a flexible strap with two ends adapted to form two closed loops, an improvement comprising:
    a. a locking mechanism located on the strap between the two ends, said locking mechanism adapted for securing one end of the strap to form a loop;
    b. an integral hinge formed in the strap between the two ends, said restraining device is the restraining device is adapted to be secured and stored in a folded position when not in use folded at the integral hinge; and
    c. a cover having a hollow interior, inner walls, a top portion and a bottom portion and open ends, said cover adapted for placement on the strap by inserting one end of the strap through the open ends of the cover, said cover is slidably mounted over said hinge and locking mechanism when in use to reinforce said hinge and preclude tampering with said locking mechanism.

2. The disposable restraining device of claim 1, an improvement further comprising an identification element for identifying a restrained individual.

3. The disposable restraining device of claim 1, said cover further including a slot in the top and bottom portions of the cover, said slots being in alignment with the central opening of each locking mechanism when the cover is in the operational, reinforcing position, whereby each end of the strap is threaded through the slots, in addition to being threaded through the central opening, when forming the loops.

4. The disposable restraining device of claim 1, said cover further including a detent system for locking the cover in either the storage position or the operational, reinforcing position.

5. The disposable restraining device of claim 1, further comprising a core material embedded in the strap and extending substantially the length of the strap, the core material having a higher melting point than the strap.

6. The disposable restraining device of claim 1, wherein the core material is a metal.

7. The disposable restraining device of claim 6, wherein the core material further comprises a wire located in the center and extending through the length of the flexible strap.

8. The disposable restraining device of claim 5, wherein the core material is a woven fiber.

9. The disposable restraining device of claim 2, wherein the identification element comprises:
    a. a permanent identification code on the flexible strap wherein said identification code is in a visible position when the strap is formed into the loops;
    b. a removable tab secured to the strap and having a front and back side; and
    c. the permanent identification code on the front side of the tab.

10. The disposable restraining device of claim 9, an adhesive material applied to the back side of the tab.

11. The disposable restraining device of claim 10, the back side of the removable tab having a removable shielding material overlying the adhesive.

12. The disposable restraining device of claim 2, wherein the identification element comprises a strip located on the strap having a write-on surface for a ball point pen, wherein said surface is in a visible position when the strap is formed into the loops.

13. The disposable retraining device of claim 1 wherein
    a. said strap is a single, molded flexible strap having a longitudinal axis, said strap also having first and second tip ends located along the axis;
    b. said locking mechanism comprises first and second locking mechanisms integrally formed with said strap and located at the median of the strap along the axis of the strap between the two ends, each locking mechanism having a slot extending therethrough, said slot being substantially perpendicular to the axis of said strap, said slot adapted for receiving and securing a tip end of the strap such that the tip end of the strap passes through the axis of the strap; and
    c. said integral hinge is located between the first and second locking mechanisms.

14. The disposable restraining device of claim 13, the strap further comprising a first and second bend, wherein the first bend is located one end of the strap and the integral hinge and the second bend is located between the other end of the strap and the integral hinge, whereby the strap may be folded at each bend in addition to folding the device in half at the integral hinge to place the strap in a folded position.

15. The disposable restraining device of claim 14, wherein at least one of said locking mechanisms located on the strap between the two ends is adapted for securing one end of the strap to form a loop, and wherein the locking mechanism has an outer pocket adapted to receive one end of the strap and form a wedge fit for securing the device in the folded position.

16. The disposable restraining device of claim 14, wherein the strap further comprises a third, fourth, fifth and sixth bend, wherein the third bend is located between the first bend and the hinge, the fourth bend is located between the second bend and the hinge, the fifth bend is located between the first bend and the end of the strap and the sixth bend is located between the second bend and the other end of the strap, whereby the strap in the folded position may be folded again at the additional bends to place the strap in a multi-folded position.

17. The disposable restraining device of claim 3, wherein the interior of the cover is adapted to receive the folded end of the strap when the cover is in the storage position, said folded end forming a wedge fit in the interior for securing the strap in the multi-folded position.

18. The disposable restraining device of claim 13, wherein the restraining device includes smooth, radiused edges for minimizing injury to a restrained person.

19. The disposable restraining device of claim 9, wherein the identification code on the strap and on the front side of the tab is identical and consists of an alpha-numeric sequence.

20. The disposable restraining device of claim 18, the saw tooth wedge surface having a first and second end, wherein the first end is connected to the resilient spring and the second end is a rounded edge for protecting the locking wedges against tampering with a pin or other pointed object thereby preventing the two ends of the strap from being withdrawn.

21. The disposable restraining device of claim 2, an improvement further comprising a material wherein the strap is made of a material having a brightly colored surface.

22. The disposable restraining device of claim 9, further including the locking mechanism comprising:
  a. a central opening extending through the strap which contains a resilient spring defining a cover over the opening of each locking mechanism for protecting the locking mechanism against tampering with a pin or other pointed object thereby preventing the two ends of the strap from being withdrawn;
  b. the locking mechanism further including the resilient spring for engaging and securing the end, an extended saw tooth wedge surface connected to the spring and projecting in toward the formed loop, the strap including two sides, both sides having a complementary saw tooth surface;
  c. a locking tooth projecting into the opening opposite from the saw tooth wedge surface and wherein the strap the wedge surface engages one side of the strap and the locking tooth engages the other side of the strap to prevent the ends from being withdrawn; and
  d. the saw tooth wedge surface having a first and second end, wherein the first end is connected to the resilient spring and the second end is a rounded edge for protecting the locking wedges against tampering with a pin or other pointed object thereby preventing the two ends of the strap from being withdrawn.

23. The disposable restraining device of claim 13, the strap further comprising:
  a. a first and second bend, wherein the first bend is located between one end of the strap and the integral hinge and the second bend is located between the other end of the strap and the integral hinge, whereby the strap may be folded at each bend in addition to folding the device in half at the integral hinge to place the strap in a folded position; and
  b. the locking mechanism having an outer pocket adapted to receive one end of the strap and form a wedge fit for securing the device in the folded position.

24. The disposable restraining device of claim 4, said detent system further comprising:
  a. at least one recess on each locking mechanism; and
  b. a corresponding protrusion on the inner walls extending into the interior of the cover, said protrusion adapted to slidably fit into said recess for detaining the cover in place.

25. The disposable restraining device of claim 24, wherein the protrusions and recesses on one locking mechanism are placed in contact with each other to lock the cover in the storage position.

26. The disposable restraining device of claim 25, wherein the protrusions and recesses on each locking mechanism are placed in contact with each other to lock the cover in the operational, reinforcing position.

27. The disposable restraining device of claim 13, wherein each locking mechanism has a central opening extending through the strap and each locking mechanism contains a resilient spring defining a cover over the opening for protecting the locking mechanism against tampering thereby preventing an end of the strap from being withdrawn.

28. The disposable restraining device of claim 13, further comprising:
  a. a first and second bend, wherein the first bend is located between one end of the strap and the integral hinge and the second bend is located between the other end of the strap and the integral hinge, whereby the strap may be folded at each bend in addition to folding the device at the integral hinge; and
  b. a third, fourth, fifth and sixth bend, wherein the third bend is located between the first bend and the hinge, the fourth bend is located between the second bend and the hinge, the fifth bend is located between the first bend and the end of the strap and the sixth bend is located between the second bend and the other end of the strap, whereby the strap in the folded position may be folded again at the additional bends to place the strap in a multi-folded position.

29. The disposable restraining device of claim 13, further comprising a material wherein the strap is made of a material having a brightly colored surface.

30. The disposable restraining device of claim 13, wherein the restraining device includes smooth, radiused edges for minimizing injury to a restrained person.

31. The disposable restraining device of claim 27, wherein each locking mechanism further includes a resilient spring for engaging and securing the end, an extended saw tooth wedge surface connected to the spring and projecting in toward the formed loop, the strap including two sides, one side having a complementary saw tooth surface whereby the two surfaces engage to prevent the ends from being withdrawn from the locking mechanism.

32. The disposable restraining device of claim 31, the locking mechanism further comprising a locking tooth projecting into the opening opposite from the saw tooth wedge surface and wherein the strap further includes a saw tooth surface on both sides whereby the wedge surface engages one side of the strap and the locking tooth engages the other side of the strap to prevent the ends from being withdrawn.

33. The disposable restraining device of claim 31, further comprising a material wherein the strap is made of a material having a brightly colored surface.

34. The disposable restraining device of claim 31, wherein the restraining device includes smooth, radiused edges for minimizing injury to a restrained person.

* * * * *